United States Patent [19]

Bickely et al.

[11] Patent Number: 5,068,638

[45] Date of Patent: Nov. 26, 1991

[54] ELECTRICAL SENSING ELEMENT

[75] Inventors: Alan C. Bickely, Sawtry Huntingdon, England; Travis Moore, Dumfries, Scotland

[73] Assignee: The Gates Rubber Company, Denver, Colo.

[21] Appl. No.: 405,484

[22] Filed: Sep. 11, 1989

[30] Foreign Application Priority Data

Sep. 14, 1988 [GB] United Kingdom ............... 8821539

[51] Int. Cl.⁵ .............................................. H01C 10/10
[52] U.S. Cl. ....................................... 338/114; 338/99
[58] Field of Search ...................... 338/114, 99, 210; 174/94 R

[56] References Cited

U.S. PATENT DOCUMENTS

| | | | |
|---|---|---|---|
| 2,472,214 | 6/1949 | Hurvitz | 338/114 |
| 2,596,420 | 5/1952 | McGarvey | 338/114 X |
| 3,794,790 | 2/1974 | Leyland | 338/114 X |
| 4,571,542 | 1/1986 | Arai | 338/114 X |
| 4,654,475 | 3/1987 | Bickley et al. | 174/94 R |
| 4,794,365 | 12/1988 | Dunbar | 338/114 X |

FOREIGN PATENT DOCUMENTS

| | | |
|---|---|---|
| 167387 | 6/1950 | Austria . |
| 1534467 | 7/1968 | France . |
| 1059522 | 2/1967 | United Kingdom . |
| 1468590 | 3/1977 | United Kingdom . |
| 2030384 | 4/1980 | United Kingdom . |
| 1587800 | 4/1981 | United Kingdom . |
| 2069251 | 8/1981 | United Kingdom . |
| 2163304 | 2/1986 | United Kingdom . |

Primary Examiner—Marvin M. Lateef
Attorney, Agent, or Firm—C. H. Castleman, Jr.; H. W. Oberg, Jr.; J. L. Isaac

[57] ABSTRACT

A sensing element includes a body of pressure sensitive electrically conductive material formed by a non-conductive matrix of flexible elastomeric material, the matrix containing electrically conductive particles. The body is formed with spaced connection regions, at least one of which is a hole into which an electrical connector may be inserted as a push fit. The connector is oversize in a direction transversely of the hole to ensure that the connector is held in place in the body and makes good electrical connection therewith.

12 Claims, 1 Drawing Sheet

ELECTRICAL SENSING ELEMENT

BACKGROUND OF THE INVENTION

1. Field of the Invention

This invention relates to a sensing element that comprises a body of pressure sensitive electrically conductive material. Many such materials have now been proposed, based on the mixing of electrically conductive particles into an electrically insulating elastomer which is subsequently shaped and cured. The resultant product is electrically non-conductive, but is rendered conductive when the material is deformed.

By incorporating a body of such material as a resistance element in an electrical circuit signals can be derived from that circuit which are related to the force applied to the body of material, either in compression or elongation.

2. Description of the Related Art

One problem that has been experienced by workers in this field has been the effective connection of electrical connectors to the body of pressure sensitive material. Such connectors should make effective electrical connection with the body of material, yet not cause significant physical damage to the body of conductive material. Furthermore, the connection should remain secure and the effectiveness of the connection, both mechanically and electrically, should not vary significantly with time.

There have in the past been proposals to sew or stitch a copper wire into the body of conductive material and to use adhesives to connect an electrical conductor to the body of material. Each of these methods has deficiencies.

SUMMARY OF THE INVENTION

According to the present invention a sensing element comprises a body of pressure sensitive electrically conductive material formed by a non-conductive matrix of flexible elastomeric material, the matrix containing electrically conductive particles, the body being formed with spaced connection regions, at least one of the connection regions being a hole into which an electrical connector may be inserted as a push fit.

The invention provides a very simple and efficient connection system, relying simply on the insertion of an electrical connector of appropriate size into the hole in the conductive body. The resilience of the body allows the connector to be inserted as a push fit and then to be firmly held by the material of the body. This ensures good electrical connection, and the relative sizes of the hole and the connector are selected to ensure that there is adequate mechanical connection over the range of conditions to which the joint will be subjected.

It will be appreciated that the body of pressure sensitive electrically conductive material may be of any shape suited to the particular environment in which it is intended to be used. Thus, the material may be in strip, sheet or block form, and, where the body is relatively thin, it may be formed with thickened sections in the spaced connection regions, the holes being formed in the thickened sections.

Particular advantage may be gained if the body is a tube, and the spaced connection regions are those parts of the bore which are located at opposite ends of the tubes. Tubular sensing elements may be used in many different environments, and may be subjected either to elongation or to transverse compression. A force of either type will give rise to a resistance change in the material from which the tube is formed.

Although a simple, unprotected tube may be usable in some cases, it will more generally be preferred to have the outer surface of the tube surrounded by electrically insulating elastomeric material. This will prevent the tube from making contact with external materials that may affect the electrical properties of the tube, and it will also give mechanical protection to the surface of the tube. However, by using a further elastomeric material for the surround the structure remains both resilient and flexible so that its potential uses are not limited.

In some cases the surround material may be chosen so that it modifies the electrical properties of the tube. Thus, for certain tube materials it has been found that the use of a high-modulus, high-shrink surround will produce a sensor with greater electrical resistance than that obtained using a low-modulus, low-shrink surround.

The material surrounding the tube may be dip-coated moulded or cast onto the tube, or it may be co-extruded with the tube material. The tube, whether or not surrounded by further elastomeric material, may also, except for the spaced connection regions, be encapsulated in a body of electrically insulating elastomeric material which holds the tube in a predetermined formation. For example, that formation may be a U-shape, and the spaced connection regions may then lie side by side at a surface of the encapsulating body. Formations other than U-shaped formations may be used, for example simple rectillinear formations or serpentine or other curved formations, depending on the application of the sensing element.

In some cases it may be desirable to have more than one tube encapsulated in a common encapsulating body.

There is a wide range of electrically conductive (which term is used herein to include semi-conductive) particulate materials that may be incorporated into the matrix. Examples are carbon (which may be in the form of carbon black), graphite (desirably in the form of fine ground artificial graphite), silicon (which is preferably undoped, chemical grade silicon powder), silver, tellurium and molybdenum disulphide. This list is not exhaustive, and generally speaking any electrically conductive powdered material may be used, either alone or in blends with other conductive materials.

The elastomeric matrix may be formed from any suitable polymeric material or blend thereof as long as it is electrically insulating and exhibits the required properties. Representative of suitable elastomers are silicone rubbers, whether of the condensation reaction, addition reaction or vinyl group-containing type, rubbery condensation polymers such as polyurethane rubber obtained by reaction of polyisocyanates with polyalkylene glycols, ethylene propylene-non-conjugated diene rubbers, natural rubber, synthetic polyisoprene rubber, styrene butadiene rubber, nitrile-butadiene rubber, halogenated hydrocarbon rubbers such as elastomeric chloroprene rubber, fluoroolefin rubber, chlorosulfonated polyethylene thermoplastic elastomers such as ethylene-vinyl acetate copolymers, and plasticizer containing thermoplastic resins.

Other non-conductive materials such as solvents, plasticising agents, stabilizers, pigments, colouring agents and extending oils may be incorporated into the composition. Such composition may contain fillers such as silica, silicates, kaolin, mica, talc, carbonates or alumina. Generally speaking, the matrix material should be compounded so that it can resist a high-intensity electric field, has good electrically insulating properties and the mechanical properties appropriate to the end use. In some cases these properties include low permanent set and high elongation at break. In other fields it may be advantageous for the matrix to be of cellular material, and any suitable blowing agent or other expanding system may then be compounded with the elastomer.

The conductive particles and any other required materials may be mixed with the elastomeric matrix material in any suitable manner. Mixing is facilitated if the matrix material is in liquid form, (whether using solvent or not) however, it is possible to effect mixing into a solid elastomer. The aim will often be to obtain a reasonably uniform dispersion of the conductive particles throughout the matrix. After mixing, a cross-linking system is added to the mixture which is then cured to any required shape. The cured material may be degassed if necessary. For many uses a room temperature vulcanising material is used, for ease in compounding and casting and for better control of particle distribution. When materials with better mechanical properties are required, however, high temperature vulcanising materials may be used. Alternatively, the properties of room temperature vulcanising materials may be improved by appropriate compounding ingredients.

When the body is to be in the form of a tube it is particularly preferred if the matrix material is a high temperature vulcanising silicone rubber, which may readily be extruded in tubular form.

When the outer surface of the tube is surrounded by electrically insulating elastomeric material, then this may again be formed from any suitable polymeric material or blend thereof that is electrically insulating and exhibits the required properties.

Preferably if oil is present in the surrounding material then that oil is incompatible with the elastomeric matrix of the pressure sensitive material so that oil migration does not occur. When the matrix material is a silicone rubber then suitable surrounding materials may include natural rubber, styrene butadiene rubber, nitrilebutadiene rubber, synthetic polyisoprene rubber and ethylene propylene-non-conjugated diene rubbers. Such rubbers may be compounded in latex form and applied simply by dipping the body of pressure sensitive conductive material, or they may be compounded so that they can be coextruded with, or otherwise extruded into contact with, that body.

BRIEF DESCRIPTION OF THE DRAWINGS

In order that the invention may be better understood specific embodiments thereof will now be described in more detail, by way of example only, with reference to the accompanying drawings in which.

DESCRIPTION OF THE PREFERRED EMBODIMENTS

Figure 1:
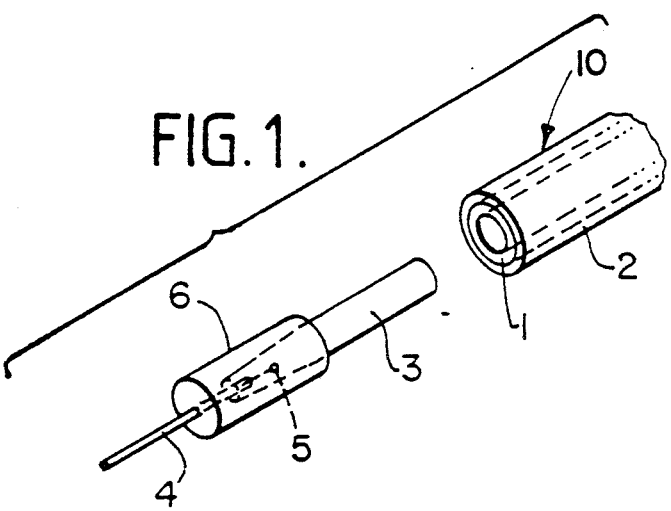
FIG. 1 is a partial perspective view of an end and connection portion of a tubular sensing element according to the invention.

Referring now to FIG. 1 this shows one end of a sensing element that comprises an inner tubular body 1 of pressure sensitive electrically conductive material, the outer surface of which is surrounded by a jacket 2 of electrically insulating elastomeric material. The tube 1 is formed by a non-conductive matrix of flexible elastomeric material, the matrix containing electrically conductive particles.

Many different types of elastomeric material can be used, but the preferred material is a high temperature vulcanising silicone rubber. The electrically conductive particles may be of any suitable conducting material, but carbon has been found particularly suitable.

In one specific example the tube was formed from a carbon-loaded silicone rubber having a specific gravity of 1.18, a tensile strength of 50 kg/cm$^2$, an elongation break of 200%, a tear strength of 10 kg/cm, a volume resistivity of 2000 ohms/cm and a Shore A hardness of 65°.

The electrical resistance of a 40 cm length of such tube is 1 Megohm, falling to 200KΩ at a 15% elongation and to 100KΩ at a 30% elongation.

The tube 1 is formed by extrusion, and the jacket 2 may be formed either by dipping the extruded tube, by coextruding the tube and jacket material, or by extruding jacket material onto the previously extruded tube.

In one example the jacket material 2 was cured natural rubber latex into which the extruded tube 1 had been dipped. The jacket material had a volume resistivity in excess of $10^{12}$ ohm cm, and was thus effectively electrically insulating.

FIG. 1 shows an electrical connector for connecting to the end of the sensing element. The connector comprises a conductive metal probe 3, to which a conductor 4 with an insulating cover is connected at 5 by a welded, soldered or other joint. An insulating body 6 covers that joint.

The relationship between the diameters of the bore of the tube 1 and of the probe are such that the probe may be inserted into the wall as a push fit, the elastomeric material of the tube being distorted during such insertion. The resilience of the material then ensures a good electrical and mechanical connection between the tube and the probe. Suitable wall diameters for the tube have been found to lie in the range of 0.5 mm to 6 mm, and each probe should be nominally oversized with respect to the bore by about 50%.

The simplicity of effecting the necessary connection will obviously be appreciated, but it has been found that the connection is substantially electrically consistent, in that values of measured resistance changes of the sensing element remain consistent even over prolonged periods of time.

The simple tubular sensing element shown in FIG. 1 may be used in many applications wherein the element is subjected either to elongation or to transverse compression in order to change its electrical resistance. However, it may be fabricated into more complex sensing elements for other applications.

Figure 2:
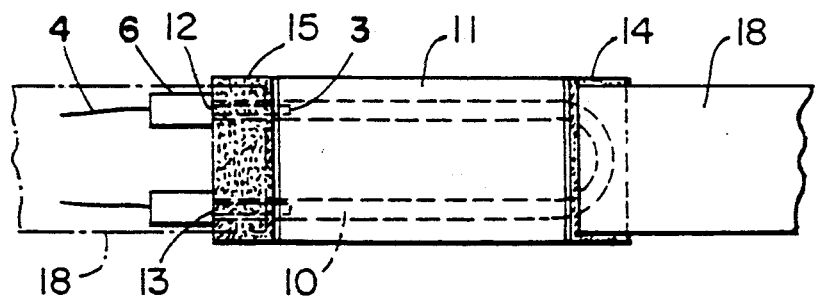
FIGS. 2 to 4 are respectively a schematic plan view, side elevation and end elevation of an embodiment of sensing element.
Figure 3:
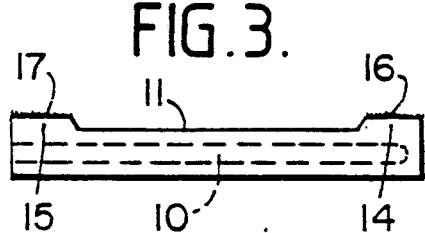
Figure 4:
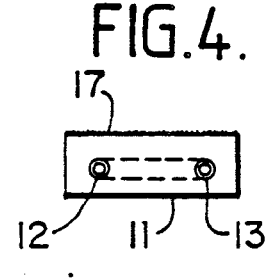

FIGS. 2 to 4 show a fabricated element that may, for example, be utilized in monitoring chest expansion during breathing. To this end, the sensing element comprises a sensing tube 10, which may be a simple extruded tube of pressure sensitive electrically conductive material, or may be a combined tube and jacket construction as shown in FIG. 1. The tube is folded to a U-shape and is encapsulated in a body 11 of electrically insulating elastomeric material, which holds the tube in the U-shaped formation. The ends 12 and 13 of the tube lie side by side at an end surface of the encapsulating body, and electrical connectors may be inserted into those ends in the manner shown in FIG. 1. One suitable material for the encapsulating body is HM prevulcanised latex from Industrial Latex Adhesives Limited, treated chemically to render it heat sensitive and then cast into a heated mold to encapsulate the tube. The cured material has a tensile strength of 38 MPa, an elongation at break of 1000% and a modulus of 0.8 MPa at 300% elongation.

The encapsulating body has enlarged end regions 14 and 15, to which pads 16, 17 of "Velcro" material may be secured, for example by adhesive bonding. Apart from providing a firm anchorage for the Velcro pads the enlarged end regions act to concentrate elongation in the narrower central region of the sensing element when this is placed under extension.

The sensing element may be employed in monitoring a patient's breathing simply by fastening a strap 18 around the chest or abdomen of the patient and securing ends of the strap having Velcro fasteners to the Velcro pads of the sensing element. The strap may include additional adjustment means if required. Conductors leading to an electrical resistance network are then simply secured to the sensing element by inserting probes on the end of the conductors into the ends 12, 13 of the tubular element. As the patient breathes, the resultant elongation and retraction of the tube of pressure sensitive conductive material causes the resistance of that tube to change, such change being monitored by the electrical network.

Figure 5:
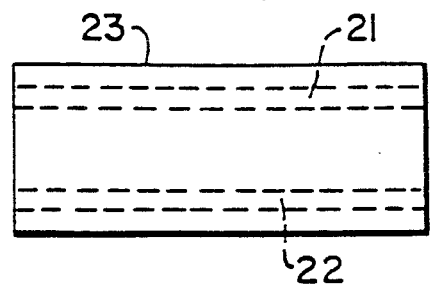
FIG. 5 is a schematic plan view of a further embodiment of a sensing element.

FIG. 5 shows an embodiment of the invention in which two tubes 21, 22 of pressure sensitive electrically conductive material are encapsulated in a common encapsulating body 23. Open ends of the bores of the tubes are exposed at opposite ends of the body, and connection may be made thereto by probes as already described. In the construction of FIG. 5 the applied force/resistance characteristics of the two tubes may be similar or different, and the electrical circuit to which they are connected may be designed accordingly. Different characteristics may, for example, give different resistance sensitivities over different ranges of applied force.

It will, of course, be understood that sensing elements in accordance with the invention need not be of the form specified in the drawings, but that they may take virtually any form and be capable of application in a number of different environments.

We claim:

1. A sensing element comprising a continuous, extruded tubular body of pressure sensitive electrically conductive material formed by a non-conductive matrix of flexible elastomeric material, the matrix containing electrically conductive particles and said tubular body having opposite open ends; and holding means holding said tubular body at two spaced locations thereof so that said tubular body is capable of axial elongation and contraction between said spaced locations, each of said open ends being exposed and forming a connection region into which an electrical connector may be inserted as a push fit.

2. A sensing element according to claim 1 in which the outer surface of said tubular body is surrounded by electrically insulating elastomeric material.

3. A sensing element according to claim 2 in which the material surrounding said tubular body is a dip-coat of electrically insulating elastomeric material.

4. A sensing element according to claim 1 in which the material surrounding said tubular body is a co-extrusion with the material of said tubular body.

5. A sensing element according to claim 1 in which said holding means comprises an encapsulating body of electrically insulating material which encapsulates said tubular body except for the spaced connection regions thereof.

6. A sensing element according to claim 5 in which said encapsulating body is of elastomeric material.

7. A sensing element according to claim 5 in which said tubular body is held in a predetermined formation by said encapsulating body.

8. A sensing element according to claim 7 in which said predetermined formation is a U-shape, and said spaced connection regions lie side-by-side at a surface of said encapsulating body.

9. A sensing element according to claim 7 in which a plurality of tubular bodies are encapsulated in a common encapsulating body.

10. A sensor system whose electrical resistance varies with the pressure applied to the system, comprising a sensing element including a continuous, extruded tubular body of pressure sensitive electrically conductive material formed by a non-conductive matrix of flexible elastomeric material, the matrix containing electrically conductive particles, and said tubular body having opposite open ends; holding means holding said tubular body at two spaced locations thereof so that said tubular body is capable of axial elongation and contraction between said spaced locations, each of said open ends being exposed and forming a connection region into which an electrical connector may be inserted as a push fit; and at least one conductor electrically connected to the sensing element, said conductor terminating at one end in a conductive probe inserted as a push fit into one of said connection regions of said tubular body.

11. A sensor system comprising a sensing element having a continuous, extruded tubular body of pressure sensitive electrically conductive material formed by a non-conductive matrix of flexible elastomeric material, the matrix containing electrically conductive particles and said tubular body having opposite open ends; an encapsulating body of electrically insulating elastomeric material, said encapsulating body encapsulating said tube except for said open ends thereof and holding said tube in a predetermined formation; said encapsulating body functioning as an anchoring means permitting secured extension or compression of said encapsulating body between two spaced regions thereby causing pressure variations to occur in said material of said tubular body; said open ends of said tubular body each forming a connection region; and an electrical resistance network, including first and second electrical conductors each terminating in a conductive probe that is inserted as a push fit into a respective one of said connection regions, said conductors being connected so that said tubular body forms one resistance in said resistance network.

12. A sensor system according to claim 11 and including fastening means connected to said encapsulating body by said anchoring means, said fastening means being such as to be capable of passing around a body to which said sensing element is to be applied.

* * * * *